US00PP34011P2

(12) United States Plant Patent
Moon

(10) Patent No.: US PP34,011 P2
(45) Date of Patent: Mar. 15, 2022

(54) ***QUERCUS* TREE NAMED 'QRMTF'**

(50) Latin Name: *Quercus rubra*
Varietal Denomination: QRMTF

(71) Applicant: Dwayne Moon, Washington, GA (US)

(72) Inventor: Dwayne Moon, Washington, GA (US)

( * ) Notice: Subject to any disclaimer, the term of this patent is extended or adjusted under 35 U.S.C. 154(b) by 0 days.

(21) Appl. No.: 17/235,606

(22) Filed: Apr. 20, 2021

(51) Int. Cl.
*A01H 6/00* (2018.01)
*A01H 5/00* (2018.01)

(52) U.S. Cl.
USPC ..... Plt./225

(58) Field of Classification Search
USPC ..... Plt./216, 225
See application file for complete search history.

*Primary Examiner* — Susan McCormick Ewoldt
*Assistant Examiner* — Karen M Redden
(74) *Attorney, Agent, or Firm* — Cassandra Bright

(57) ABSTRACT

A new and distinct *Quercus rubra* tree named 'QRMTF' is disclosed, characterized by dark green mature foliage and a significant red flush on new growth, which occurs through the Summer. Trees have been observed to have good heat tolerance in the Southern United states and a rapid growth rate. The new variety is a *Quercus* tree, typically used for landscapes and gardens.

4 Drawing Sheets

Latin name of the genus and species: *Quercus rubra.*
Variety denomination: 'QRMTF'.

BACKGROUND OF THE INVENTION

The new cultivar is a product of a planned breeding program. The new variety was discovered growing as a seedling among a group of crossbred *Quercus rubra* trees at a tree farm in Washington, Ga. The inventor made this discovery in the Summer of 2013. The exact seed and pollen parents cannot be identified.

Asexual reproduction by grafting of the new cultivar 'QRMTF' was first performed during February of 2014 at a farm in Washington, Ga. The cleft grafting system developed by the inventor has resulted in progeny that have proven the characteristics of the new variety to be genetically stable. This grafting process involved taking cuttings in February, being grafted, and being placed in calloused chambers for approximately three weeks. They are then moved into 3"×6" tree band pots and placed in humidity chambers for approximately four weeks. Furthermore, these observations have confirmed that the new variety represents a new and improved variety of *Quercus rubra* tree as particularly evidenced by the superior heat tolerance. These genetic traits can be consistently reproduced by asexual propagation.

SUMMARY OF THE INVENTION

The cultivar 'QRMTF' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'QRMTF' grown in Washington, Ga. These characteristics in combination distinguish 'QRMTF' as a new and distinct *Quercus rubra* cultivar:

1. Darker green foliage than typical for species.
2. Fast growth rate
3. Significant red flush on new growth, continuing through the Summer months.
4. Heat tolerance observed in Southern United States.

PARENT COMPARISON

The exact parent varieties cannot be identified.

COMMERCIAL COMPARISON

Plants of the new cultivar 'QRMTF' are similar to plants of *Quercus rubra* 'Aurea' (unpatented), in most horticultural characteristics, however, plants of the new cultivar 'QRMTF' differ in the following:

1. The new variety produces red new foliage; this comparator produces yellow new foliage.

Plants of the new cultivar 'QRMTF' are similar to plants of *Quercus rubra* 'Splendens' (unpatented), in most horticultural characteristics, however, plants of the new cultivar 'QRMTF' differ in the following:

1. Fall color of the new variety is a different shade of red than this comparator.
2. The new variety produces new foliage with a distinctive red coloration which continues through the Summer months.

BRIEF DESCRIPTION OF THE PHOTOGRAPHS

Figure 1:
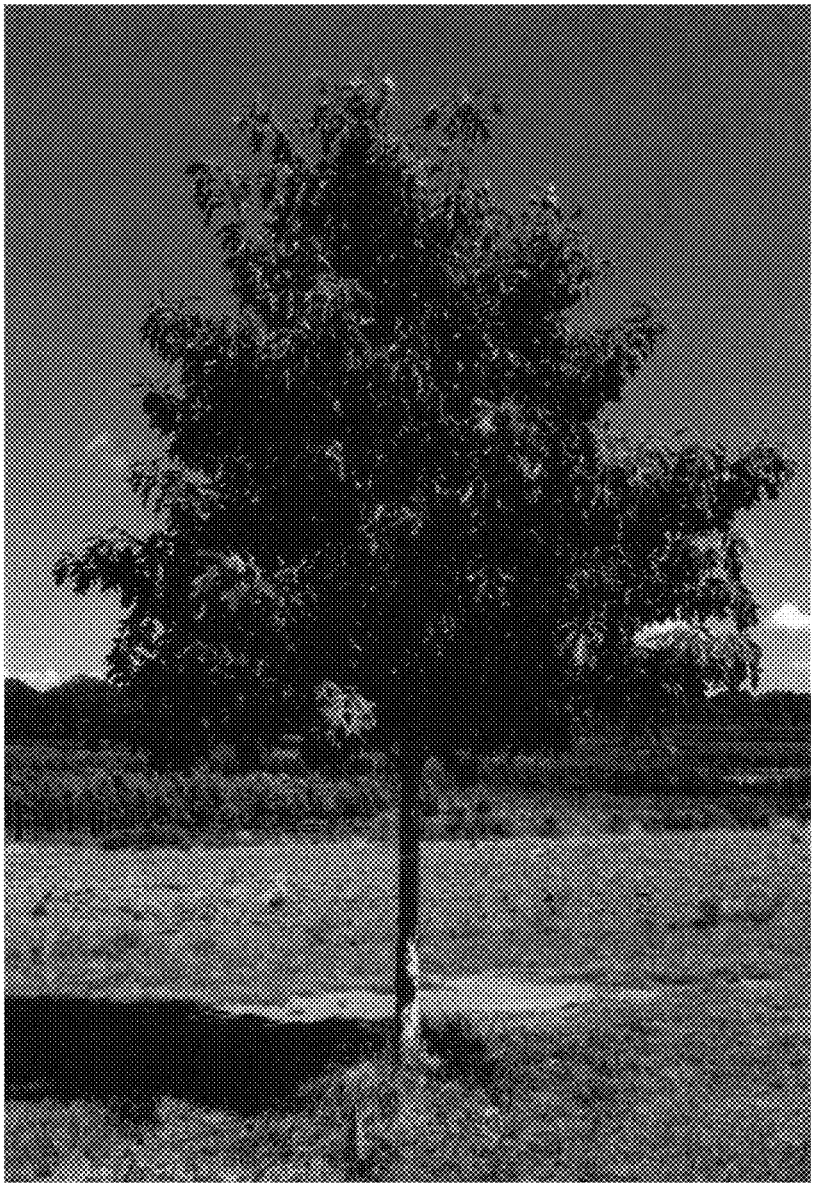

The accompanying photograph in FIG. 1 illustrate a fully leafed tree with new growth in a field, during late June. The red flush of new growth can be seen.

Figure 2:
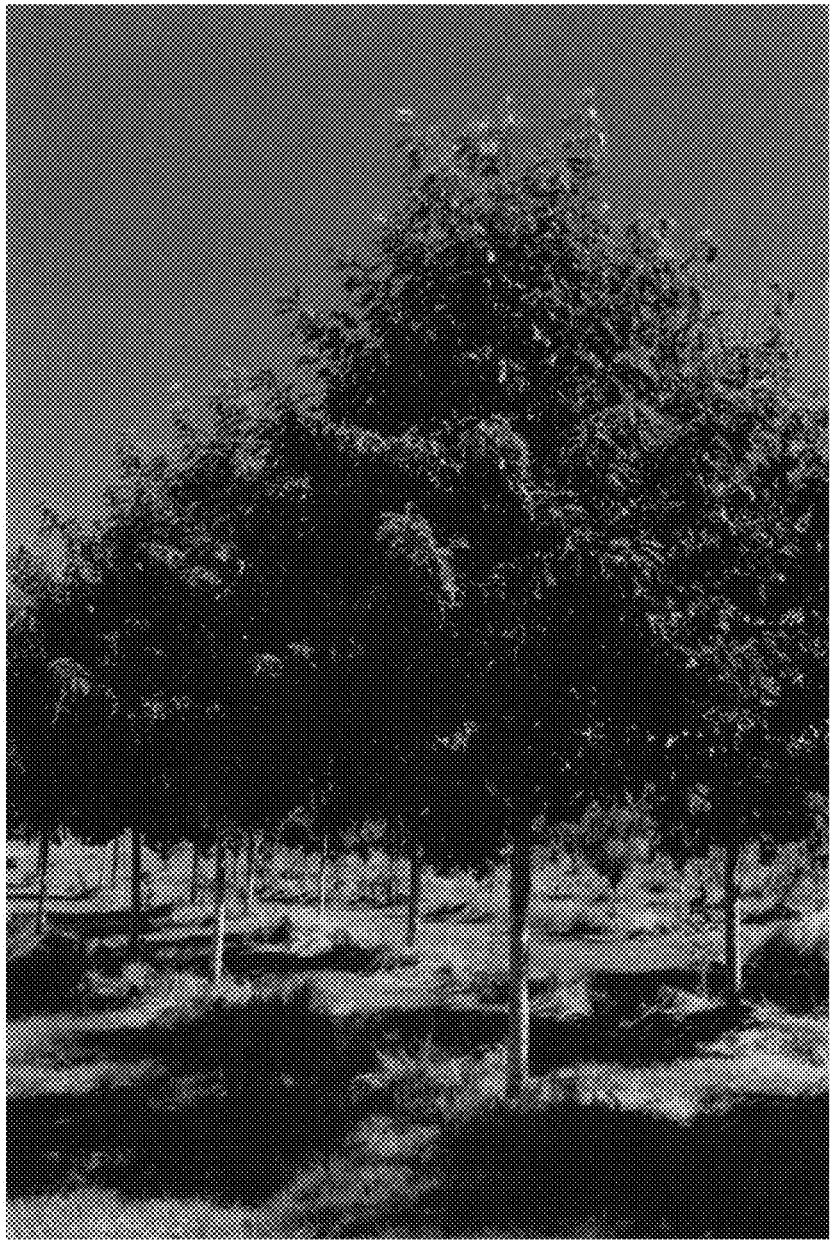

FIG. 2 illustrates a row of field trees of the new variety during early Summer, the consistency of the new foliage color is illustrated.

Figure 3:
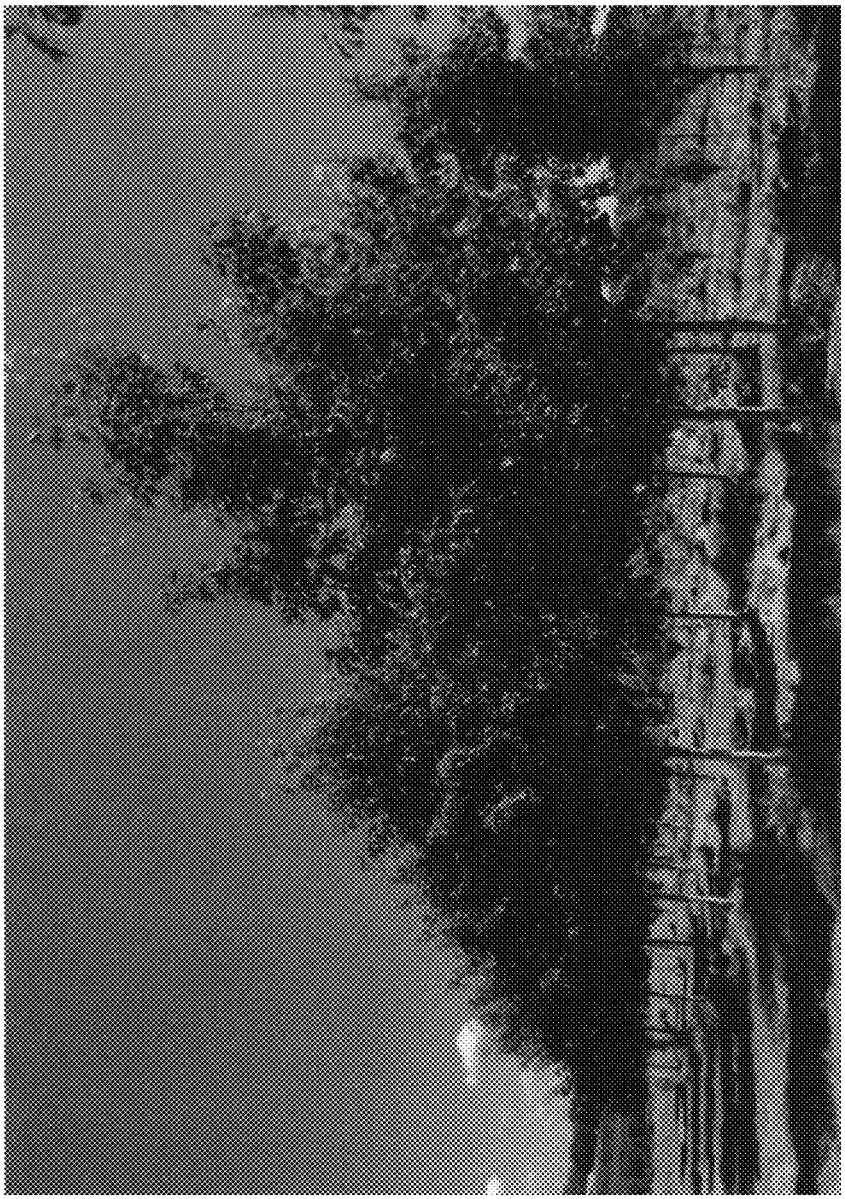

FIG. 3 illustrates a row of trees during late June. The tree in the front of the row, without a red foliar flush is an unnamed comparator *Quercus rubra*, the trees behind this comparator are the new variety. In FIG. 3 the increased amount of new red growth is seen, compared to a typical *Quercus rubra*.

Figure 4:
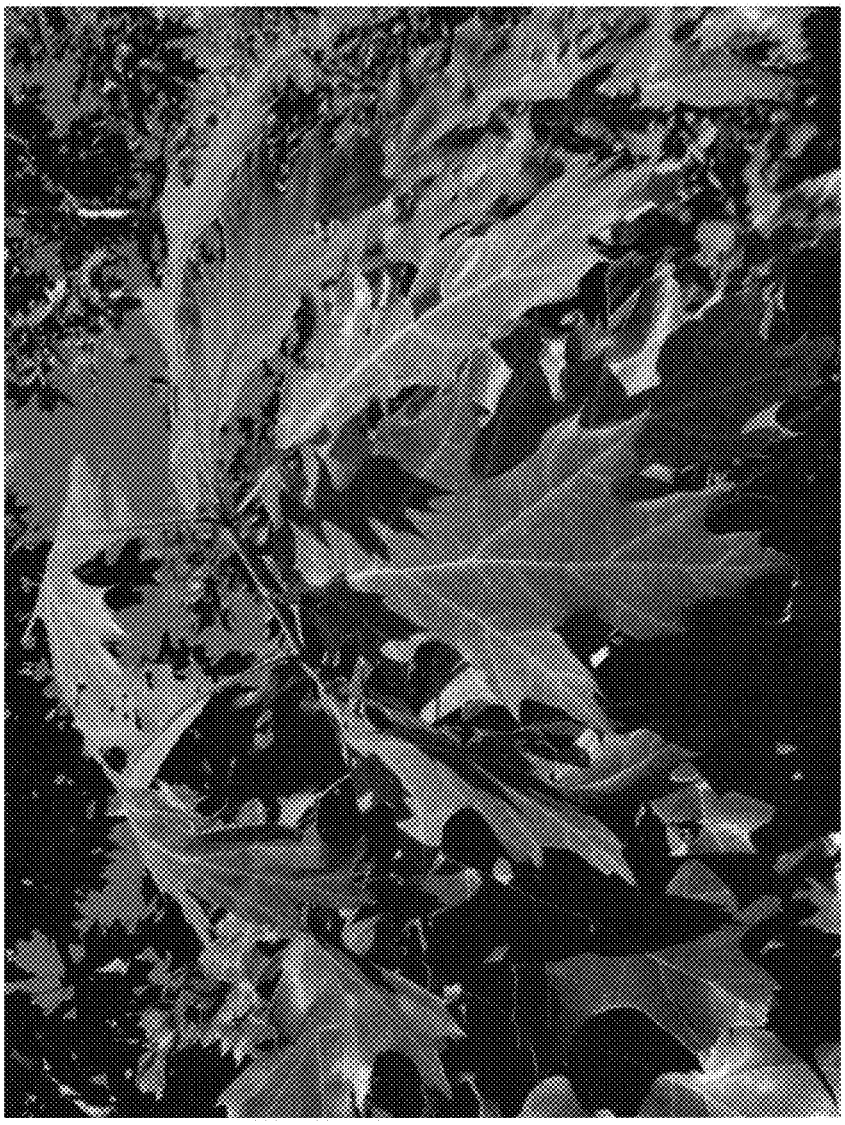

FIG. 4 illustrates a close-up view of the foliage, including the red new flush.

All trees illustrated are field grown in Washington, Ga. Trees in FIGS. 1, 2 and 3 are approximately 3 years from planting into the field, 4 years old from grafting. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'QRMTF' plants grown outdoors and in a nursery in Washington, Ga. Plants are approximately 2 years old, in a 3 gallon nursery container. Temperatures ranged from 5° C. to 10° C. at night to 18° C. to 27° C. during the day. Measurements and numerical values represent averages of typical plant types.

Botanical classification: *Quercus rubra* 'QRMTF'.

PROPAGATION

Cleft grafting.

Root description: Woody. Brown roots not accurately measured with an R.H.S. Colour chart.

PLANT

Growth habit: Deciduous tree with a broad pyramidal to round canopy.

Height: Approximately 14 feet at 3 years.

Spread: Approximately 3 feet at 3 years.

Branch aspect and angle: Branches about 45 degrees from center. Straight to slightly curved.

Growth rate: Rapid.

Trunk characteristics:

*Diameter*.—About 3 inches measured at approximately 3 inches above soil level at 3 years.

*Color*.—Near RHS Greyed-Green 198C blotched 198A.

*Surface texture*.—Rough, bark not yet formed.

*Lenticel color*.—Near RHS Greyed-Green 198D.

FOLIAGE

Leaf:

*Arrangement*.—Alternate.

*Shape*.—Overall ovate, deeply lobed, 7 to 9 loves.

*Average length*.—Approximately 12 to 20 cm excluding petiole.

*Average width*.—Approximately 7 cm.

*Apex*.—Acute.

*Base*.—Obtuse or asymmetrical cordate.

*Margin*.—Deeply lobed with sharp tips at the apex of each lobe. Sinuses about 1.2 to 2.8 cm deep.

*Texture of top surface*.—Glabrous.

*Texture of lower surface*.—Glabrous.

*Color*.—Young foliage: Upper side: Near RHS Orange-Red 34B flushed Greyed-Orange N172C, veins near Yellow 2A. Under side: Near RHS Orange-Red 34C, veins near Yellow-Green N144B. Mature foliage: Upper side: Near RHS Green 137A. Under side: Near RHS Green 137D. Fall foliage: Upper side: Greyed-Red N170A overall heavily flushed Orange-Red N30A. Under side: Greyed-Orange 174A over all heavily flushed Orange-Red N30A.

*Venation*.—Type: Pinnate. Color (mature): Venation color upper side: Near RHS Yellow-Green 145B. Venation color under side: Near RHS Yellow-Green N144A.

*Petiole*.—Length: Average 2 to 4 cm. Diameter: Average 4 mm. Texture: Glabrous. Color: Upper side: Near RHS Yellow-Green 145A. Under side: Near RHS Yellow-Green 144C.

FLOWER

Not observed.

REPRODUCTIVE ORGANS

Not observed.

OTHER CHARACTERISTICS

Disease/pest resistance: Neither resistance nor susceptibility to normal diseases and pests of *Quercus* has been observed.

Drought tolerance: No tolerance for drought observed. *Quercus rubra* is moderately drought tolerance once established.

Temperature tolerance: USDA Zones 5 through 9. Observed tolerant of hot Summer conditions in Georgia.

Fruits/nuts: Not observed.

What is claimed is:

1. A new and distinct cultivar of *Quercus rubra* tree named 'QRMTF' as herein illustrated and described.

* * * * *